US00PP32956P2

(12) United States Plant Patent
Van Swieten

(10) Patent No.: US PP32,956 P2
(45) Date of Patent: Apr. 6, 2021

(54) ***PHALAENOPSIS* ORCHID PLANT NAMED 'PHALGETWO'**

(50) Latin Name: ***Phalaenopsis* hybrid**
Varietal Denomination: PHALGETWO

(71) Applicant: ANTHURA B.V., Bleiswijk (NL)

(72) Inventor: Martinus Nicolaas Gerardus Van Swieten, Utrecht (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 16/941,650

(22) Filed: Jul. 29, 2020

(51) Int. Cl.
*A01H 6/62* (2018.01)
*A01H 5/02* (2018.01)

(52) U.S. Cl.
USPC ..... Plt./311

(58) Field of Classification Search
USPC ..... Plt./311
See application file for complete search history.

*Primary Examiner* — Annette H Para
(74) *Attorney, Agent, or Firm* — Jondle & Associates, P.C.

(57) ABSTRACT

A new and distinct variety of *Phalaenopsis* plant named 'PHALGETWO', particularly characterized by white, flecked and shaded flowers with red-purple lips, flower longevity on the plant of about 17 weeks, moderately compressed petals, flat flower shape in lateral view, and is propagated by meristem tissue culture, is disclosed.

3 Drawing Sheets

Genus and species: *Phalaenopsis* hybrid.
Variety denomination: 'PHALGETWO'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHALGETWO'.

The new *Phalaenopsis* plant is a product of a planned breeding program conducted by the inventor in Bleiswijk, the Netherlands. The objective of this breeding program was to create a new *Phalaenopsis* plant with attractive, white, flecked and shaded flowers with red-purple lips, suitable for potted plant production.

The new *Phalaenopsis* plant 'PHALGETWO' is a result of cross-pollination made by the inventor in March 2010 in Bleiswijk, the Netherlands, of the proprietary female, or seed parent, *Phalaenopsis* hybrid '01-2167' (unpatented) with the proprietary male, or pollen parent, *Phalaenopsis* hybrid '20155-01' (unpatented).

The new *Phalaenopsis* was selected by the inventor as a single plant within the progeny of the stated cross-pollination in a controlled greenhouse in Bleiswijk, the Netherlands, in February 2013. Asexual reproduction of the new *Phalaenopsis* plant by meristem tissue culture since 2014 in Bleiswijk, the Netherlands, has demonstrated that the new variety reproduces true to type with all of the characteristics, as herein described, firmly fixed and retained through successive generations.

Community Plant Variety Rights for this variety have been applied for in the European Union on Apr. 26, 2018 (Application no. 2018/1197), by Applicant who obtained the subject matter disclosed directly from the inventor. 'PHALGETWO' has not been made publicly available or sold anywhere in the world prior to the effective filing date of this application with the exception of sales or disclosures made one year or less before the effective filing date of this claimed invention by Applicant who obtained 'PHALGETWO' directly from the inventor.

SUMMARY OF THE INVENTION

The following are the most outstanding and distinguishing characteristics of this new cultivar when grown under normal horticultural practices in Bleiswijk, the Netherlands, and can be used to distinguish 'PHALGETWO' as a new and distinct variety of *Phalaenopsis* plant:

1) White, flecked and shaded flowers with red-purple lips;
2) Flower longevity on the plant is about 17 weeks;
3) Petals are moderately compressed; and
4) Flower shape in lateral view is flat.

DESCRIPTION OF THE PHOTOGRAPHS

This new *Phalaenopsis* plant is illustrated by the accompanying photographs which show the overall plant habit including blooms, buds, and foliage of the plant; the colors shown are as true as can be reasonably obtained by conventional photographic procedures. The photographs were taken in a greenhouse in Bleiswijk, the Netherlands, from 50-week-old plants in June 2020. Colors in the photographs may differ from the color values cited in the detailed botanical description, which accurately describe the actual colors of the new variety.

DESCRIPTION OF THE NEW VARIETY

Figure 1:
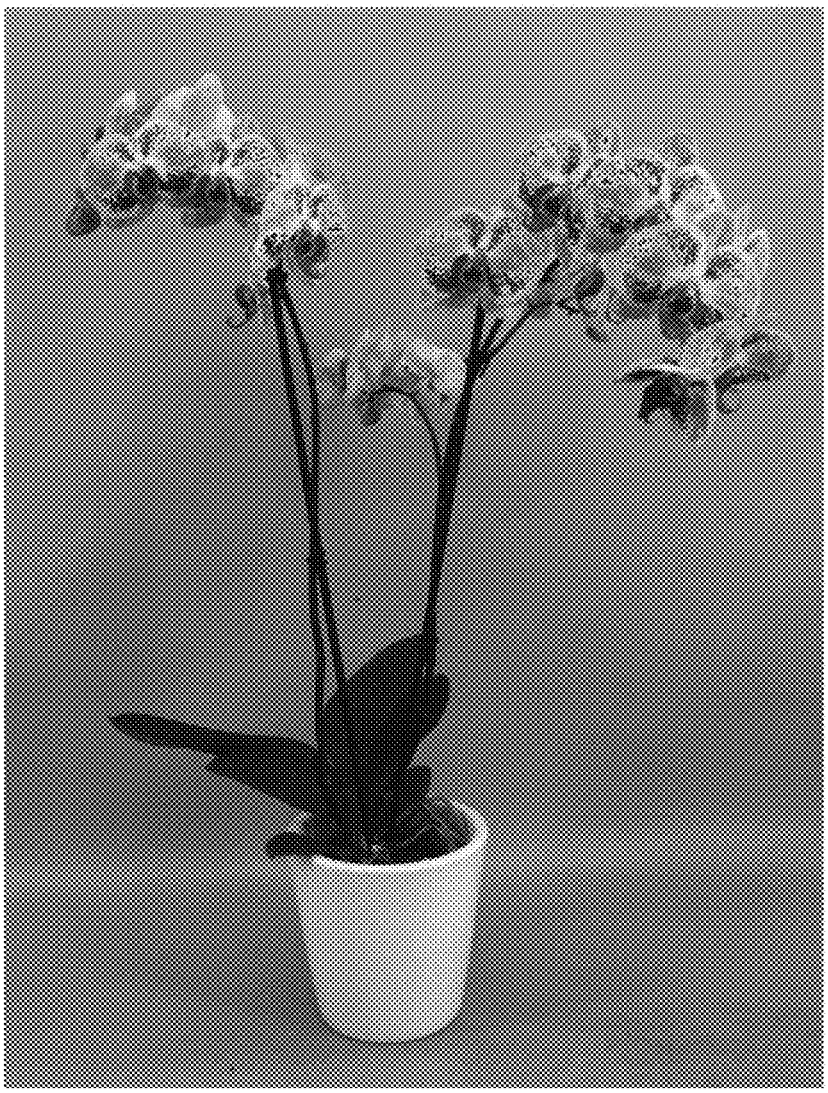
FIG. 1 shows the overall plant habit, including blooms, buds, and foliage of 'PHALGETWO'.
Figure 2:
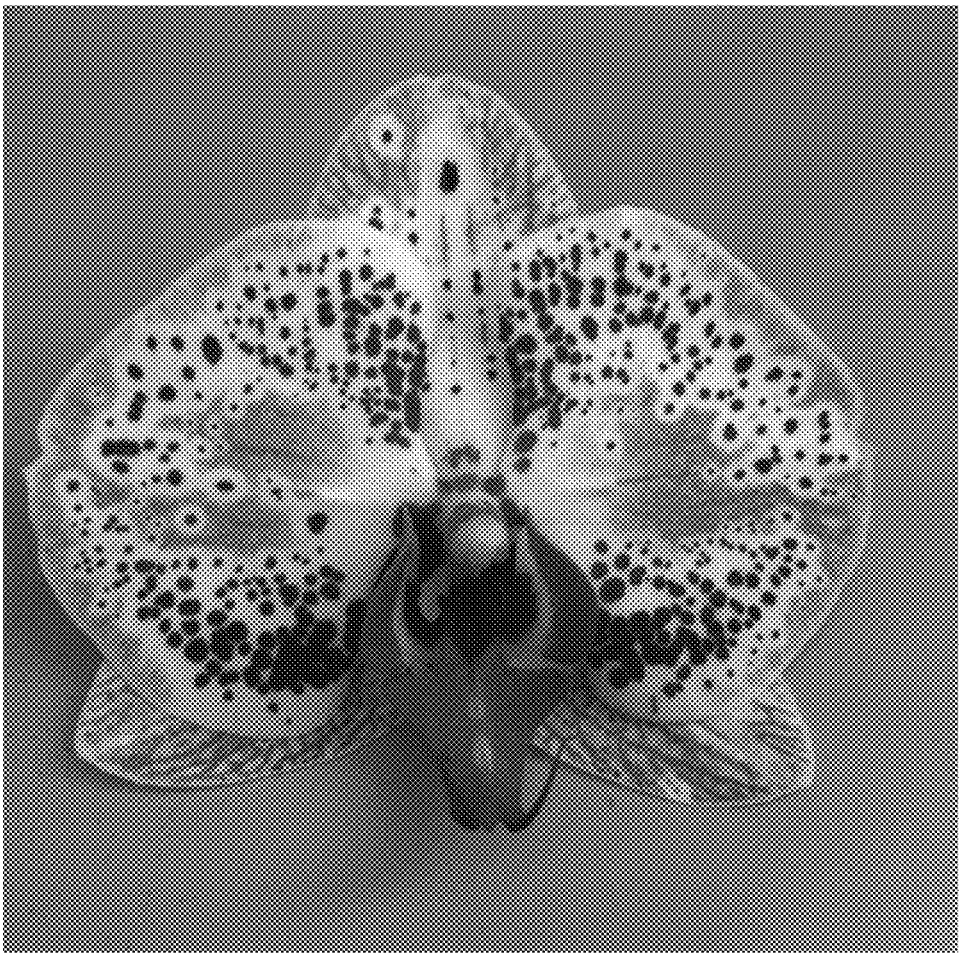
FIG. 2 shows a close-up of a flower of 'PHALGETWO'.
Figure 3:
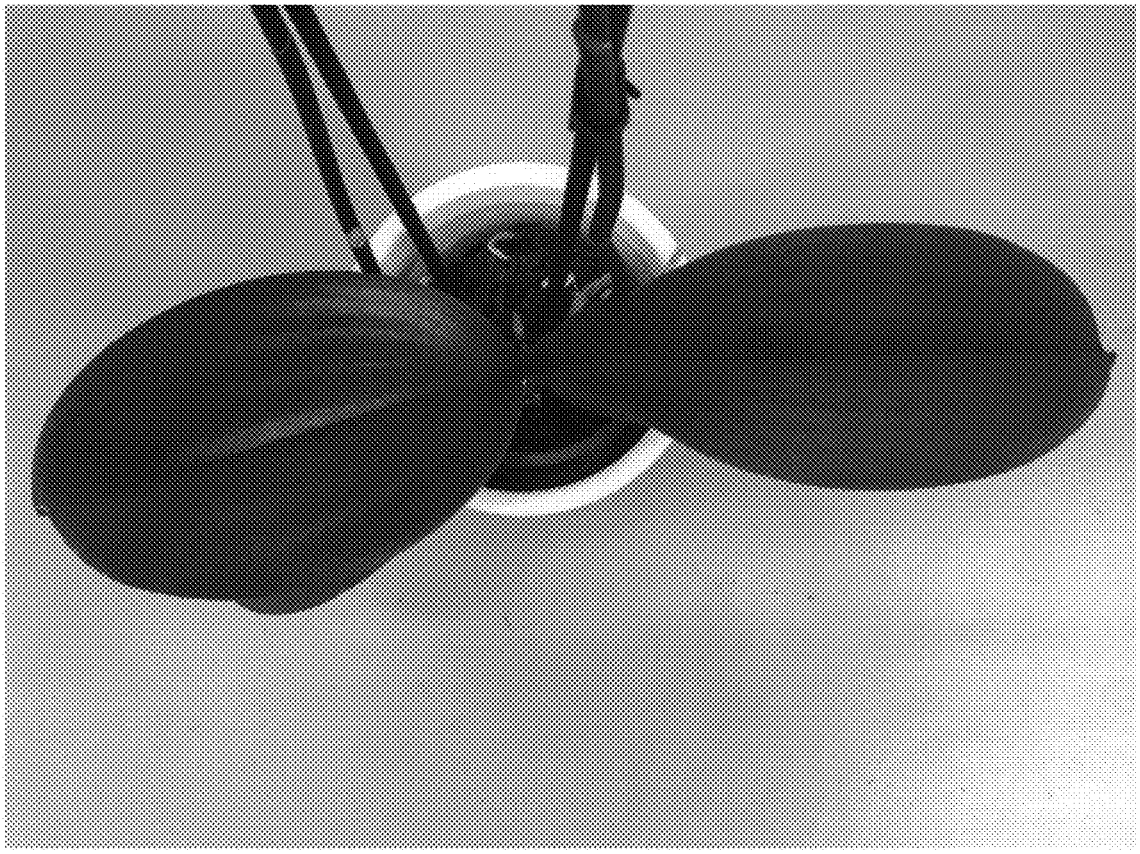
FIG. 3 shows an overhead view of the leaves of 'PHALGETWO'.

The following detailed description sets forth the distinctive characteristics of 'PHALGETWO'. Plants of the new

*Phalaenopsis* have not been observed under all possible environmental conditions. The phenotype may vary somewhat with variations in environment such as temperature, light intensity and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, the Netherlands. Observations and measurements were made in June 2020 on flowering plants which were planted in 12-centimeter (diameter) pots. After in vitro propagation, the plants were grown in nursery trays for 20-24 weeks, followed by transplantation to 12-centimeter pots and grown in a greenhouse between 27° C. to 29° C. for 30 weeks, continued by a cooling period of 8 weeks between 18° C. to 20° C. and 12 weeks in a greenhouse of 21° C. Flowering occurs after 50 weeks in 12-centimeter pots.

DETAILED BOTANICAL DESCRIPTION

Classification:

*Family*.—Orchidaceae.

*Botanical*.—*Phalaenopsis* hybrid.

*Common name*.—Moth orchid.

*Variety name*.—'PHALGETWO'.

Parentage:

*Female parent*.—*Phalaenopsis* cultivar '01-2167' (unpatented).

*Male parent*.—*Phalaenopsis* cultivar '20155-01' (unpatented).

Propagation:

*Type*.—Meristem tissue culture.

Roots:

*Root description*.—Greyed-green (something between RHS 190B and 190C) colored roots with branching lateral roots having yellow-green (RHS N144A) colored root tips.

Plant:

*Commercial crop time to flowering*.—Following asexual propagation (in vitro), the rooted cuttings grow for 20-24 weeks. After transplantation into 12-cm pots, the plants are finished after 48 to 50 weeks.

*Growth habit of the peduncle*.—Upright to slightly pendent with raceme and panicle inflorescence.

*Height* (*from soil level to top of inflorescence*).—Approximately 56.0 cm to 61.0 cm.

*Width* (*measured from leaf tips*).—About 29.0 cm to 31.0 cm.

*Vigor*.—Strong.

Leaves:

*Mature leaves*.—Quantity per plant: 6 to 8 leaves are produced before flowering. Length (fully expanded): 15.0 cm to 19.0 cm. Width: 8.0 cm to 9.0 cm. Position of the broadest part of the leaf: At the middle. Shape: Oblong. Base shape: Moderately elongated. Apex: Obtuse to rounded unequal. Leaf blade angle with the petiole (measured from the horizontal position): Between 20 degrees and 40 degrees. Leaf margin: Entire. Color: Upper surface: RHS 146A. Lower surface: RHS 146B with a reddish-brown margin (RHS 200B) toward the tip. Texture (both upper and lower surfaces): Smooth. Thickness: 2.5 mm to 2.9 mm. Variegation: Absent. Venation: Pattern: Parallel. Color of the midvein: Upper surface: RHS 146A. Lower surface: RHS 146B.

Peduncle:

*Quantity per plant*.—1 to 2.

*Number of flowers per peduncle*.—9 to 18.

*Length*.—56.0 cm to 61.0 cm.

*Diameter*.—5.0 mm to 6.0 mm.

*Strength*.—Strong.

*Aspect*.—Upright to slightly pendent.

*Texture*.—Smooth.

*Color*.—Reddish-brown (RHS 200B).

*Internode length*.—3.0 cm to 4.0 cm.

Inflorescence description:

*Appearance*.—Upright to slightly pendent, raceme and panicle inflorescence with bilaterally symmetrical flowers that open in succession beginning with the lowermost flower.

*Number of inflorescences*.—1 to 2.

*Inflorescence size*.—Height (from base to tip): 180.0 mm to 340.0 mm.

*Flowering time*.—First flowers can be expected 10 to 11 months after planting in a 12-cm pot.

*Flower*.—Height: 80.0 mm to 85.0 mm. Diameter: 90.0 mm to 95.0 mm. Depth of lip: 27.0 mm to 29.0 mm.

*Flower longevity*.—On the plant: 16 to 18 weeks.

*Flower shape*.—Flat.

*Fragrance*.—Absent.

*Flower bud*.—Average size: Large. Length: 23.0 mm to 25.0 mm. Width: 19.0 mm to 21.0 mm. Shape: Egg shaped. Color: Light yellow-green (something in between RHS 145B and 145C) at the base with a hint of purplish-red (RHS N77B).

*Petals*.—Arrangement: Open/free. Shape: Semi-circular. Apex: Emarginated asymmetric. Margin: Weakly undulated. Length (from base to tip): 44.0 mm to 46.0 mm. Width: 57.0 mm to 59.0 mm. Position of the broadest part of the petal: Toward the base. Color (when fully opened): Upper surface: Basic color: White (RHS NN155C). Over color: Purplish-pink shade (RHS N78C). Lower surface: Basic color: White (RHS NN155C). Over color: Light reddish-purple shade and margin (RHS N78D) toward the tip; diluting dark purplish-red flecks (RHS N79B). Number of spots, flecks, and stripes on the petals (upper surface): Many flecks. Color of spots, flecks, and stripes on the petals (upper surface): Something in between RHS N79B and N79C. Density of netting of the petals (upper surface): None. Color of the netting (upper surface): None.

*Dorsal sepal*.—Shape: Elliptic. Apex: Emarginated symmetric. Margin: Entire. Length (from base to tip): 46.0 mm to 48.0 mm. Width: 34.0 mm to 36.0 mm. Position of the broadest part of the dorsal sepals: At the middle. Color (when fully opened): Upper surface: Basic color: White (RHS NN155C). Over color: Reddish-purple shade (RHS N78B). Lower surface: Basic color: Light reddish-purple (RHS N78D). Over color: White (RHS NN155C) toward margin on one side; diluting dark purplish-red flecks (something in between RHS N79B and N79C). Number of spots, flecks, and stripes on the dorsal sepals (upper surface): Medium flecks; few stripes. Color of spots, flecks, and stripes on the dorsal sepals (upper surface): Flecks are something in between RHS N79B and N79C; stripes are RHS N78B. Density of netting of the dorsal sepals (upper surface): Low. Color of the netting: RHS N78B.

*Lateral sepals*.—Shape: Ovate. Apex: Obtuse asymmetric. Margin: Weakly undulated. Length (from base to tip): 49.0 mm to 51.0 mm. Width: 30.0 mm to 32.0 mm. Position of the broadest part of the lateral sepals: Toward the base. Color (when fully opened): Upper surface: Basic color: White (RHS NN155C). Over color: Reddish-purple region (RHS N78B) toward the tip. Lower surface: Basic color: Light reddish-purple (RHS N78D). Over color: Light yellow-green (RHS 145D) at the base; reddish-purple midvein (RHS N78B) toward the tip; diluting dark purplish-red flecks (RHS N79B). Number of spots, flecks, and stripes on the lateral sepals (upper surface): Medium flecks. Color of spots, flecks, and stripes on the lateral sepals (upper surface): Something in between RHS N79B and N79C. Density of netting of the lateral sepals (upper surface): Low to medium. Color of the netting (upper surface): RHS N78B.

*Labellum* (*lip*).—Whiskers: Present. Length of whiskers: 18.0 mm to 20.0 mm. Color of whiskers: Dark purplish-red (RHS N79C). Pubescence on the lip: Absent.

*Lateral lobe*.—Shape: Type V (as described in the International Union for the Protection of New Varieties of Plants (UPOV) Test Guidelines for *Phalaenopsis*); spatulate. Margin: Undulated (widely wavy). Length: 20.0 mm to 22.0 mm. Width: 14.0 mm to 16.0 mm. Color: Upper surface: White (RHS NN155C); touch of yellow (RHS 12A) on one side toward the base; reddish-purple (RHS N78A) toward the margin. Lower surface: White (RHS NN155C) at the base; touch of diluting purplish-red (RHS N77D) on one side and yellow (RHS 12B) on the other side; reddish-purple (RHS N78B) toward margin. Number of spots and stripes on the lateral lobe: Few stripes at the base. Color of spots and stripes on the lateral lobe: Dark red (RHS 183B and 187C). Density of netting of the lateral lobe: None. Color of the netting: None.

*Apical lobe*.—Shape: Triangular. Margin: Entire. Length: 20.0 mm to 22.0 mm. Width: 19.0 mm to 21.0 mm. Color: Upper surface: Hint of yellow (RHS 12A) at the base; red wings (RHS 60A); reddish-purple (RHS N78A) toward whiskers. Lower surface: Hint of yellow (RHS 12B) at the base; red wings (RHS 60A); reddish-purple (something in between RHS N78A and N78C) toward whiskers; white middle vein (RHS NN155C). Number of spots, dots, and stripes on the apical lobe: Few very small dots at the base. Color of spots, dots, and stripes on the apical lobe: RHS 184A. Density of netting of the apical lobe: None. Color of the netting: None.

*Callus*.—Average size: Medium to large. Height: 7.0 mm to 8.0 mm. Length: 6.0 mm to 7.0 mm. Width: 4.0 mm to 5.0 mm. Color: Dark red-brown (something in between RHS 187A and 200C); light greenish-yellow (RHS 4C) on sides.

Reproductive organs:

*Column*.—Length: 8.0 mm to 10.0 mm. Diameter: 5.8 mm to 6.3 mm. Color: White (RHS NN155C) at the base and reddish-purple (RHS N78B) toward the tip.

*Pollinia*.—Quantity: 2. Diameter: 0.9 mm to 1.1 mm. Color: Orange-yellow (RHS 23A).

*Ovary*.—Length: 13.0 mm to 15.0 mm. Diameter: 2.1 mm to 2.4 mm.

*Pedicel*.—Length: 38.0 mm to 40.0 mm. Diameter: 2.5 mm to 2.9 mm. Texture: Smooth. Color: Dark red-brown (something in between RHS 187A and 200B) at the base; light yellow-green (RHS 145A) and light reddish-purple (RHS N78D) toward the flower.

Disease, pest, and stress resistance: No specific resistance or susceptibility observed to pathogens and pests common to *Phalaenopsis* to date.

Fruit and seeds: Fruit and seed development has not been observed on plants of the new *Phalaenopsis* to date.

COMPARISON WITH PARENTAL LINES AND MOST SIMILAR VARIETIES

'PHALGETWO' differs from female parent plant '01-2167' (unpatented) in that 'PHALGETWO' has smaller flowers than '01-2167'.

'PHALGETWO' differs from male parent plant '20155-01' (unpatented) in that 'PHALGETWO' has flowers with a flecked and shaded pattern, whereas '20155-01' has flowers with a striped pattern. Additionally, 'PHALGETWO' has larger flowers than '20155-01'.

'PHALGETWO' is most similar to the commercial *Phalaenopsis* plants named 'PHALDASYH' (U.S. Plant Pat. No. 27,341) and 'PHALGYQXH' (U.S. Plant Pat. No. 31,132). 'PHALGETWO' differs from the commercial variety 'PHALDASYH' in that 'PHALGETWO' has spatulate lateral lobes and triangular apical lobes, whereas 'PHALDASYH' has weakly spatulate lateral lobes and rhombic apical lobes. Additionally, 'PHALGETWO' has larger flowers and longer whiskers than 'PHALDASYH'.

'PHALGETWO' differs from the commercial variety 'PHALGYQXH' in that 'PHALGETWO' has oblong leaves and emarginated petal apexes, whereas 'PHALGYQXH' has obovate leaves and rounded petal apexes.

I claim:

1. A new and distinct variety of *Phalaenopsis* plant named 'PHALGETWO', substantially as described and illustrated herein.

* * * * *